United States Patent
Krishna et al.

(10) Patent No.: US 10,933,208 B2
(45) Date of Patent: Mar. 2, 2021

(54) ASTHMA INHALER ACCESSORY

(71) Applicants: Vandana M. Krishna, Winchester, MA (US); Sampath Krishna, Winchester, MA (US); Neal S. Krishna, Winchester, MA (US); Ryan N. Krishna, Winchester, MA (US)

(72) Inventors: Vandana M. Krishna, Winchester, MA (US); Sampath Krishna, Winchester, MA (US); Neal S. Krishna, Winchester, MA (US); Ryan N. Krishna, Winchester, MA (US)

(*) Notice: Subject to any disclaimer, the term of this patent is extended or adjusted under 35 U.S.C. 154(b) by 434 days.

(21) Appl. No.: 15/351,072

(22) Filed: Nov. 14, 2016

(65) Prior Publication Data

US 2018/0133417 A1    May 17, 2018

(51) Int. Cl.
*A61M 15/00* (2006.01)

(52) U.S. Cl.
CPC ...... *A61M 15/0086* (2013.01); *A61M 15/009* (2013.01); *A61M 15/0021* (2014.02); *A61M 15/0088* (2014.02); *A61M 2205/02* (2013.01); *A61M 2205/0227* (2013.01); *A61M 2205/0238* (2013.01); *A61M 2205/13* (2013.01); *A61M 2205/273* (2013.01); *A61M 2205/582* (2013.01); *A61M 2205/583* (2013.01); *A61M 2205/6081* (2013.01)

(58) Field of Classification Search
CPC .......... A61M 15/0086; A61M 15/0021; A61M 2205/583; A61M 15/0088; A61M 15/009; A61M 2205/273; A61M 2205/02; A61M 2205/0227; A61M 2205/6081; A61M 2205/13; A61M 2205/0238; A61M 2205/582

See application file for complete search history.

(56) References Cited

U.S. PATENT DOCUMENTS

| | | | | |
|---|---|---|---|---|
| 4,470,412 A | * | 9/1984 | Nowacki | A61M 15/0086 128/200.18 |
| 4,534,343 A | | 8/1985 | Nowacki et al. | |
| 4,674,491 A | * | 6/1987 | Brugger | A61M 11/06 128/200.14 |
| 4,796,614 A | | 1/1989 | Nowacki et al. | |
| 4,809,692 A | * | 3/1989 | Nowacki | A61M 15/0086 128/203.29 |
| 4,852,561 A | | 8/1989 | Sperry | |

(Continued)

OTHER PUBLICATIONS

Thayer Medical LiteAire, http://thayermedical.com/products/liteaire/, captured May 20, 2020.*

(Continued)

*Primary Examiner* — Theodore J Stigell

(57) ABSTRACT

A hollow extension tube or extension assembly aids in increasing the quantity of any inhaled or aerosolized substance delivered to a patient's lungs from an inhaler or source. The length of the extension tube reduces the velocity and increases the temperature of the aerosolized substance, easing inhalation. The interior surface of the hollow extension tube has anti-static properties which reduces the amount of aerosolized substance trapped by the interior surface of the hollow extension tube. The interior surface of the extension tube may be formed of cardboard.

7 Claims, 5 Drawing Sheets

(56) References Cited

U.S. PATENT DOCUMENTS

| | | | | |
|---|---|---|---|---|
| 4,926,852 | A | * | 5/1990 | Zoltan ................ A61M 15/0086 128/200.23 |
| 4,953,545 | A | * | 9/1990 | McCarty ........... A61M 15/0086 128/200.14 |
| 5,012,803 | A | | 5/1991 | Foley et al. |
| 5,012,804 | A | | 5/1991 | Foley et al. |
| 5,042,467 | A | * | 8/1991 | Foley ................ A61M 15/0086 128/200.14 |
| 5,178,138 | A | * | 1/1993 | Walstrom .......... A61M 15/0086 128/200.14 |
| 5,477,849 | A | * | 12/1995 | Fry .................... A61M 15/0086 128/200.14 |
| 5,505,194 | A | | 4/1996 | Adjei et al. |
| 5,522,383 | A | * | 6/1996 | Calvert ............. A61M 15/0028 128/203.15 |
| 5,746,197 | A | * | 5/1998 | Williams ............ A61M 15/009 128/200.23 |
| 5,839,430 | A | * | 11/1998 | Cama .................. A61B 5/0871 128/200.14 |
| 5,904,139 | A | | 5/1999 | Hauser |
| 5,964,417 | A | * | 10/1999 | Amann ............. A61M 15/0028 128/203.21 |
| 6,679,252 | B2 | * | 1/2004 | Sladek ............... A61M 15/0086 128/200.22 |
| 2003/0010336 | A1 | * | 1/2003 | Vito .................. A61M 15/0086 128/200.22 |
| 2003/0073930 | A1 | * | 4/2003 | Morrissey ............ A61F 13/141 600/573 |
| 2008/0035142 | A1 | * | 2/2008 | Lulla ................. A61M 15/0086 128/203.12 |
| 2008/0210225 | A1 | * | 9/2008 | Geiger .............. A61M 15/0086 128/200.14 |
| 2009/0032019 | A1 | * | 2/2009 | Green ................... A61M 16/06 128/203.29 |
| 2010/0163045 | A1 | | 7/2010 | Powell et al. |
| 2013/0276781 | A1 | * | 10/2013 | Steelman .......... A61M 15/0086 128/203.12 |
| 2014/0251321 | A1 | * | 9/2014 | Benson ............... A61M 15/009 128/200.23 |
| 2015/0174343 | A1 | * | 6/2015 | Muellinger ............ A61M 11/06 128/200.16 |
| 2016/0250437 | A1 | * | 9/2016 | Fink ...................... A61M 16/14 128/200.14 |
| 2017/0232212 | A1 | * | 8/2017 | Bruin .................. A61M 15/002 128/203.12 |
| 2019/0151578 | A1 | * | 5/2019 | Dennis .............. A61M 15/0088 |

OTHER PUBLICATIONS

Franklin et al., "Aerosolized Steroids in Bronchial Asthma", *Journal of Allergy*, 29(3), May 1958.

Gomm et al., "Effect of an Extension Tube on the Bronchodilator Efficacy of Terbutaline Delivered from a Metered Dose Inhaler", *Thorax*, (35) 1980.

Sheth et al., "In Vitro Evaluation of Nonconventional Accessory Devices for Pressurized Metered-Dose Inhalers", *Annals of Allergy, Asthma, and Immunology*, 113(1), May 2014.

* cited by examiner

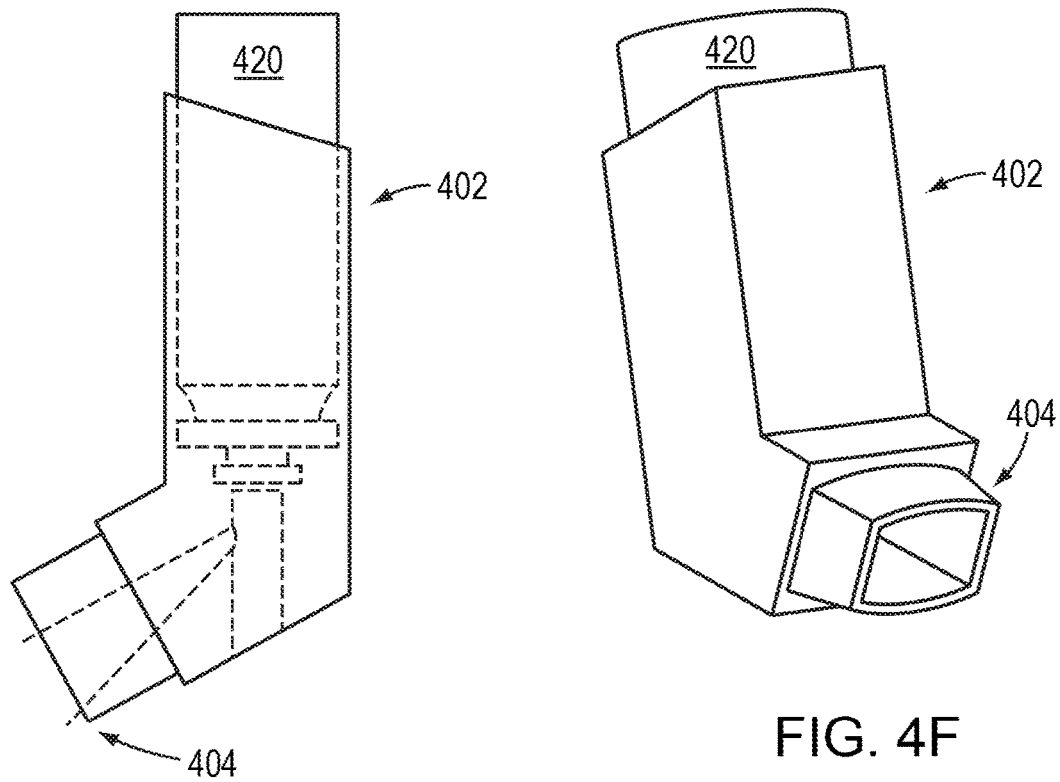
FIG. 4E
FIG. 4F
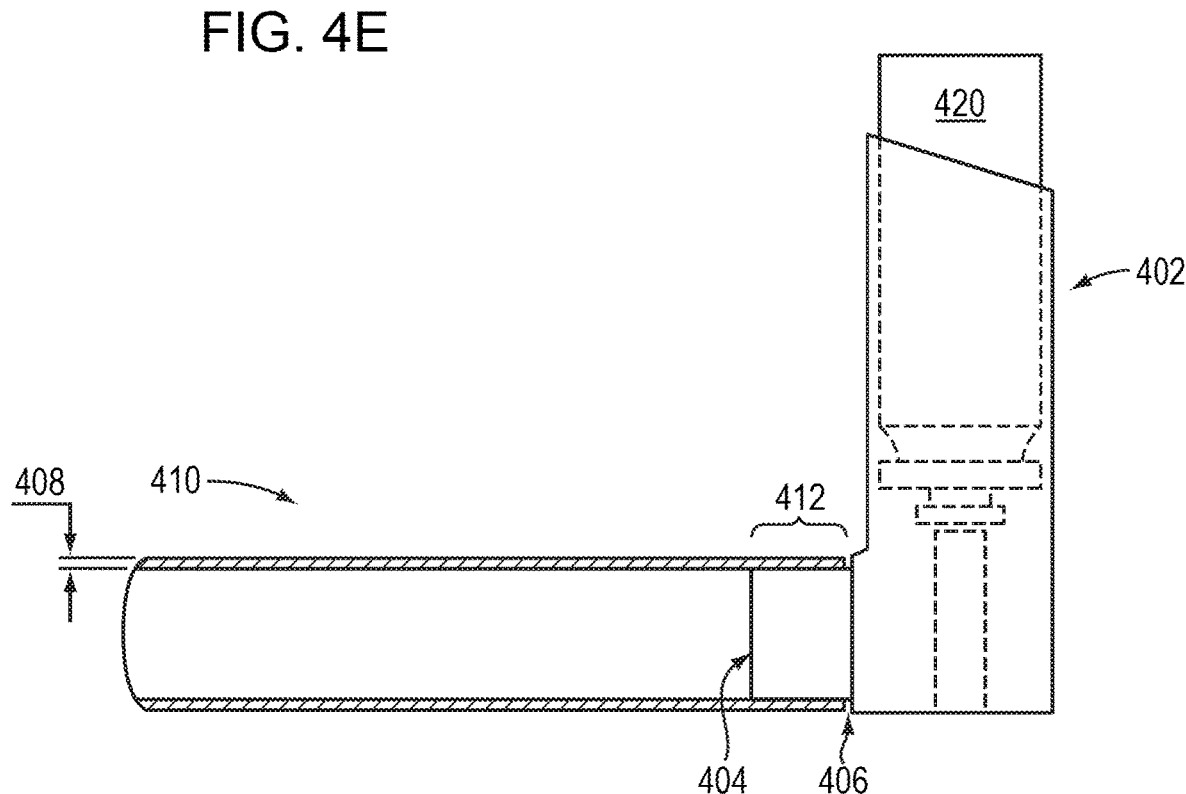
FIG. 4G

ASTHMA INHALER ACCESSORY

FIELD OF INVENTION

The present invention relates to accessory devices for delivering aerosolized drugs, vaccines, and other inhaled substances, including but not limited to dry powders, soft mist, pressurized metered aerosolized medicines, smoking pipes, and breath analyzers.

BACKGROUND

Patients suffering from asthma and other respiratory disorders are often prescribed inhalers, a device that is designed to deliver a precise amount of aerosolized drug or medication directly to the lungs. Inhaled medications for asthma and COPD are available as pressurized metered-dose inhalers (pMDI or MDI), breath-actuated MDIs, dry powder inhalers (DPI), and Nebulizers. These are collectively referred to as MDI hereon. These drug delivery devices suffer from many shortcomings, such as high cost, cumbersome usage techniques, need for precise coordination, and breath control. It is estimated that up to 50% of the medication never reaches the lungs and gets deposited in the throat. This residual medicine may have other side effects on the teeth, throat, and the mucosal membrane.

Typically, a MDI has an actuator, a nozzle, and a mouthpiece (outlet/supply port). The user inserts or otherwise positions (assembles generally) a pressurized canister into the MDI. The pressurized canister contains the drug suspended in a mixture of propellants, preservatives, surfactants, flavoring and dispersing agents. These canisters under pressure commonly use hydrofluoroalkane (HFA) as the propellant.

The patient self-administers the MDI by placing their mouth tightly around the mouthpiece and inhaling exactly when the MDI canister is actuated. Depending upon the inhalation device, the technique differs. For example, pMDIs require one to take a slow deep breath whereas DPIs require a forceful deep breath. These techniques require training, practice, and precise coordination, which are confusing and difficult for patients, especially the pediatric and geriatric population. The force of ejection from the nozzle reduces the temperature of the ejected amount of medicine. Finally, the throat may instinctively close due to the impact from the delivered mass of medicine, further reducing the drug delivery to the lungs. The medication that is deposited in the oropharynx may lead to undesirable side-effects.

To overcome these shortcomings, many suppliers have developed extension devices such as spacers and valved holding chambers that can be used in conjunction with an MDI. The principal goal of these extension devices is to partially compensate for poor technique and improve medication delivery to the lungs by reducing the deposition in the oropharynx.

The purpose of a spacer/holding chamber is to reduce the velocity and the force of impaction of the aerosolized medication on the throat. A holding chamber also allows sublimation of the propellants, reduces particle size, and raises the temperature.

Most current medication delivery systems are complex and expensive devices that cost $20-$100 each and require a medical prescription. The delivery system device is expected to be used by the patient multiple times. These devices are not easily collapsible, disposable, transferable, or labeled for reuse by another patient. They frequently incorporate complex arrangements of valves, holding chambers, inlet and outlets that make their use cumbersome, often requiring training and/or assistance.

These delivery system devices tend to be bulky (6 to 12 inches long and 2-3 inches in diameter) often made of plastic or similar material with a holding chamber for the medication.

The plastic holding chambers are often triboelectric on the inside walls (i.e., inner wall surface), which attracts the aerosol droplets that are transporting the medicine from the inhaler. Some of the medication thus adheres to the inside wall of the plastic holding chamber. As a result, a suboptimal dose of medication reaches the lungs. As time passes, more medication might be deposited on the inner wall surface in the holding chamber, and the amount of medication output from the device becomes variable.

A typical asthmatic patient is prescribed to use the inhaler, and thus the delivery system device, twice a day. The patient uses it more often during an emergency or physically demanding situations. The existing extension devices are intended for multiple uses and therefore expected to be kept clean. Thus, the user is instructed to clean the plastic holding chamber after each use. Manufacturers recommend washing and air drying after each use. The recommended method for drying existing devices is to air-dry or drip-dry; this potentially reduces the static build up inside the chamber. The user is also instructed to not use any cloth or paper to wipe dry, the rubbing action can build up static electricity and can change the amount of the next dose of medication delivered to the lungs. The static effect is more pronounced in cold weather when the air holds less moisture, resulting in further reduced delivery of medication with potentially life-threatening consequences. Due to these cumbersome instructions and inherent disadvantages, the patient compliance is estimated to be low and the cleaning technique suspect at best.

There also exist other forms or versions of these delivery device systems for pediatric use, which feature a mask that fits on the face and cover the mouth and nose. There is evidence that the children dislike the mask or find it scary on their face and having to breathe through it. There is also an added risk of deposition of inhaler aerosol into the eyes and nose due to leakage away from the oral cavity.

The difficulty multiplies many fold in rapid turnover mobile health units, such as acute care facilities in a busy city, war zones, post-disaster recovery areas, etc., where the local populace or our troops may be exposed to respiratory irritants or toxic gases. This situation calls for a large supply of inhalers and spacer devices, so that many (plural) patients can be treated quickly in order to avoid respiratory collapse and further complications from acute bronchial constriction.

The state of the art delivery system devices feature variations in size, mask attachments, configurations, and ports. The availability of multiple choices makes it difficult for the prescriber to choose the right extension type accessory for the patient as there is no standardization or information on the advantages of one spacer over another. There is a long standing need for a simpler, portable, disposable device that achieves the same goals (and would be a useful addition to the physician's arsenal).

SUMMARY OF THE INVENTION

Embodiments of Applicant's invention described herein overcome the above discussed shortcomings and disadvantages of the prior art with an elegant solution that is effective, simple, portable, cheap, and non-threatening. One embodiment employs a paper or cardboard tube of a variable length and diameter that fits snugly (e.g., morphs to fit) over the delivery system/MDI device's outlet/supply port on one end, and that fits in the patient's mouth on the other end. Specifically, Applicant's invention envisions multiple embodiments described below without limitation.

In embodiments, a single use, disposable hollow extension luminal tube is open at both ends, and is in the shape of a cylinder or conical frustum that serves to reduce average particle size and the velocity of medication particles emerging from an MDI nozzle.

In another embodiment, the hollow extension tube may have one or more telescoping sections to increase or reduce the length of the tube. The telescoping version of the tube not only serves to reduce the speed and particle size of the ejected mass of medicine, it also changes the operable diameter to be received by the patient's mouth. The telescoping sections may have an indentation, groove, or a ridge to prevent the different sections of the tube from separating.

In embodiments, the hollow extension tube is indicated for single use and made of cardboard or similar material that is non-static, minimizes triboelectric charge buildup, is nontoxic, and is biodegradable.

In another embodiment, the hollow extension tube is made of flexible but semi-rigid material that enables the user to easily deform (or morph) the lumen to fit different shaped inhalers or other outlets. The tube may be stored flattened or carried in a handbag, backpack or bag.

In embodiments, the hollow extension tube is of such length that sufficiently slows down the medication but not so long as to make the MDI or delivery system inconvenient to use.

In embodiments, the exterior surface of the hollow extension tube may display printed usage instructions.

In embodiments, the hollow extension tube may have indicators (such as notches or holes) at one end to differentiate between the end that fits the delivery system device and the end that inserts into the user's mouth.

These and other advantages and features will be made clear in the following detailed description.

Generally speaking, embodiments of the present invention provide a spacer/extension device comprised of a hollow tube, in the shape of a cylinder or conical frustum. The tube has dimensions of a length, an inner diameter (uniform along the length in some embodiments), an outer diameter (uniform along the length in some embodiments), and a wall thickness (uniform along the length in some embodiments). Along the length of the tube, an interior surface defines the interior of the tube. The tube also has an exterior surface along the length that defines the exterior of the tube. One end of the tube may be referred to as a front end (proximal or first end) that is spaced across the length of the tube and opposite from a back end (distal or second end).

The walls of the hollow tube are gas impermeable. The gas impermeable nature of the tube/extension device allows for aerosolized medicine (medicaments) to be transferred across (along) the length of the tube, through the interior of the tube, without the medicine dispersing. The front end of the tube can be removably coupled to a source of medicine (e.g., to the outlet or mouthpiece of an MDI); and the back end of the tube is placeable inside a patient's mouth. This allows for a dose of medicine to be properly delivered (at an acceptable particle size and optimal velocity) across the length of the tube, through the interior of the tube, from the source of medicine to the patient. However unlike the prior art, the interior surface of the tube possesses anti-static properties that reduces triboelectric charge buildup. Because triboelectric charge buildup is reduced, the interior surface does not interfere with or diminish the amount of medicine delivered while the tube effectively reduces (throttles) velocity and the particle size of the plume (due to evaporation or sublimation of excipients, propellants, and such) of aerosolized medicine.

In one embodiment, at least the interior surface of the tube is comprised of cardboard, paper, or other material having anti-static properties. In other embodiments, the extension device is comprised of a cardboard tube. In further embodiments, the exterior surface of the tube is comprised of a different material than the interior surface. The exterior surface may be coated with plastic, wax, or the like to improve grip, mouth feel, texture for the mouth, user experience, and/or sanitation. The exterior surface does not require anti-static properties necessarily.

In embodiments, the extension device/tube is designed for single use (disposable). A disposable extension device/tube avoids the necessary, lengthy, difficult cleaning and sanitation process that a reusable tube requires. A single use extension device allows for quick utilization and disposal, simplifying use.

In some embodiments, the tube back end, the tube front end, or both are identified by a visual or tactile indicator to help avoid contamination during disposal or other handling of the tube. The visual or tactile indicator may be printed usage instructions, a label, an arrow, a symbol, a graphic, a hole, an indentation, a notch, or the like.

At least the front end of the tube is composed of semi-rigid material that is sufficiently elastic and/or deformable (flexible) to partially engulf (or be engulfed by) or at least slip on and encircle a supply port (outlet) of the source of medicine when the front end is fitted to the supply port. In some embodiments, the front end of the tube is sufficiently elastic and/or deformable (flexible) to partially engulf, be engulfed by, or slip on and encircle a supply port by taking on the shape of the supply port or by being reshaped (morphed) thereby. For non-limiting example, the front end of the tube initially having a circular cross section, is able to morph and take the shape of an ellipse, a rectangle (with rounded corners), or an oval in order to engulf, be engulfed by, or slip on and encircle a supply port (i.e., MDI outlet) with a cross-section of that shape. In some embodiments, the tube may be formed of a semi-rigid material sufficiently elastic and/or deformable to be flattened or similarly contorted in order to ease storage.

In some embodiments, the extension device/tube is removably coupled to the source of medicine only using friction. When the tube front end partially engulfs (or encircles) the supply port (or outlet) of the source of medicine, the extension device is held in place only by the friction between the interior surface at the front end of the tube and the exterior surface of the supply port. The friction force is of sufficient strength to keep the extension device and source of medicine coupled during administration/operation of the source without the use of clips or other additional securing mechanisms. Because no clips or other securing mechanisms are needed to keep the extension device connected to the source of medicine, the tube and source of medicine may be removably coupled or decoupled by a simple push-on/pull-off operation. The push-on pull-off operation and friction only coupling allows for quick, simple, and easy use. This is important when there is a need to deliver medicine to a patient quickly or to a large number of patients efficiently.

Embodiments provide a method and apparatus of facilitating the delivery of medicine. The method comprises providing a hollow gas impermeable tube, having a front (first) end spaced across a length of the tube from a back (second) end. Further the tube has an interior surface forming a wall about an interior space and possessing anti-static cling properties. Next, the method enables removably coupling a source of medicine at the front (first) end of the tube and the back (second) end of the tube being placeable inside a patient's mouth. Finally, the method allows for facilitating the transfer of an amount of medicine, in a gas or aerosolized form, across the length of the tube, through the interior space of the tube, from the source of medicine to the patient.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 4E is a side perspective view of a typical source of medicine, such as an MDI. FIG. 4F is an isometric perspective view of a typical source of medicine, such as an MDI. FIG. 4G is a partially cut away, illustrating the coupling of the extension device embodiment, of FIG. 4A, to the subject source of medicine, of FIG. 4E, in assembled state.

DETAILED DESCRIPTION OF THE INVENTION

A description of example embodiments of the invention follows.

Applicants describe an assembly formed of a hollow extension tube that is non-static, single-use, disposable, inexpensive, portable, and recyclable, through which adult and pediatric inhaler-users inhale the medication directed towards their lungs.

Embodiments use the hollow extension tube to deliver aerosolized medication from a canister such as pressurized Metered Dose Inhaler (MDI), soft mist inhaler (SMI), dry powder inhaler (DPI), placebo inhaler devices or gas substances to/from other devices such as smoking pipes such as hookahs, breath analyzers, spirometers, peak flow meters, training devices, demonstration devices, etc. These delivery system devices are collectively or generally referred to herein as an "Inhaler" and/or "the source of medicine." Restated, embodiments provide a compact, convenient, portable and unobtrusive add-on device to MDIs/inhalers.

It has been estimated that 28-68% of patients do not use their MDI correctly or proficiently enough to benefit from the prescribed medication. Inadequate medication delivery leads to more emergency room visits, and urgent care visits often at a high cost to the patient and the health care system. The nature of the disease states requiring aerosolized medications such as asthma/COPD often exacerbates acutely leading to urgent care visits culminating in prolonged hospital admissions and billions of dollars for medical management, lost productivity and missed days of work and school. The present invention can prevent critical errors in drug delivery and increase the efficiency of aerosolized delivery.

Extension devices of the present invention, when combined with MDIs, compensate for poor inhalation technique, reducing medication deposition in the throat and pharynx, and increasing lung deposition. Applicants' extension devices improve the clinical effect of inhaled medications. Embodiments also provide a softer, warmer feel on the back of the throat by producing a softer impact and avoiding the cold Freon effect of a blast of propellant hitting the back of the throat and responsively stopping any further inhalation. This stoppage of further inhalation can cause a critical error in drug delivery by stopping further airflow to carry any drug or medicine into the lungs.

Physical Dimensions

Embodiments of the present invention provide a hollow extension tube 100, 200, 300. One end (the proximal end) of the tube 100, 200, 300 removably couples to a subject MDI (or other inhaler device/source of medicine) outlet and the opposite end (distal end) of tube 100, 200, 300 goes into the patient's mouth. The inner diameter of the tube is carefully chosen to fit somewhat snugly (morph) around the outlet. The inner diameter is also chosen to ensure a reasonably tight fit on many presently available MDI/inhaler devices.

Figure 1:
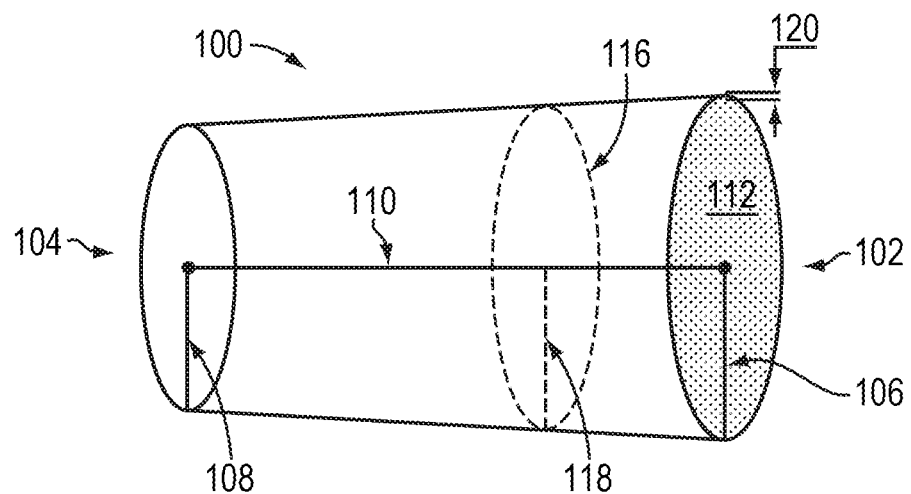
FIG. 1 is a schematic view of an extension device embodying the present invention and comprising a tube in the shape of a hollow conical frustum.

FIG. 1 is a schematic view of an extension device embodying the present invention. The extension device comprises a tube 100 in the shape or form of a hollow conical frustum. Tube 100 has a length 110 between a front end 104 and a back end 102. Front end 104 is circular in shape with a front radius 108. Back end 102 is circular in shape with a back radius 106. Where the back radius 106 is larger than the front radius 108, tube 100 has a taper along its length from back end 102 to front end 104. In a like manner, the inner circumference 116 of tube 100 tapers from back end 102 to front end 104 where wall thickness 120 of the tube 100 is uniform. The value of inner circumference 116 is controlled by inner radius 118 that has an upper limit of back radius 106 and a lower limit of front radius 108. Tube 100 possesses wall thickness 120 and has an interior (inner) wall surface 112. The tube wall surrounds and otherwise defines the inner space of tube 100.

Figure 2:
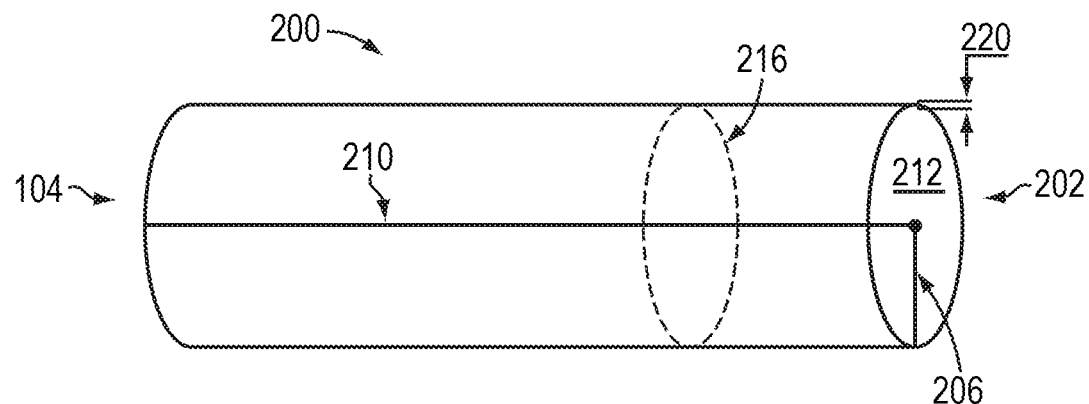
FIG. 2 is a schematic view of another embodiment formed of a tube in the shape of a hollow cylinder.

FIG. 2 is a schematic view of an extension device of the present invention comprising a tube 200 in the shape of a hollow cylinder. That is to say, in some embodiments, tube 200 is in the form of a hollow cylinder. Tube 200 has length 210 between front end 204 and back end 202. Front end 204 is circular in shape with a radius 206. Back end 202 is circular in shape of the same size as that of front end 204 and hence with a same radius 206. Thus tube 200 has uniform inner circumference 216 along length 210 and has no taper. Tube 200 possesses wall thickness 220. Tube 200 has interior (inner) wall surface 212.

Accordingly, the hollow extension tube 100, 200 may be constructed of uniform inner diameter, as in a cylinder, or have a taper toward the proximal end 104, as in a conical frustum, to aid the coupling of that end to the outlet of the MDI/inhaler. The other end (distal end) 102 is dimensioned to fit conveniently into the patient's mouth. The taper may be of such dimensions that it does not make it inconvenient to the person taking the medication, i.e., the patient or user. The taper may be in either direction, narrow end on the outlet of the MDI/inhaler or in the mouth of the patient, to ensure a good fit at both ends.

It is understood, that tube 100, 200, 300 (detailed below) may be made of different sizes and dimensions, including but not limited to, wall thickness, length, inner diameter, outer diameter, taper, inner circumference, etc. For non-limiting example, in one embodiment, tube length is about 6 cm-14 cm, outer diameter is about 2 cm-5 cm, and wall thickness is about 0.01 mm-2 mm.

Basic Functionality and Properties

Tube 100, 200, 300 is made of or comprises cardboard material. The cardboard is biodegradable and minimizes static buildup on inner wall surface 112, 212. The cardboard material and relatively thin wall thickness 120, 220 (e.g., about 0.01 mm-2 mm) enable either tube front end 104, 204 or tube back end 102, 202 to deform in a manner morphing and/or conforming to the cross-sectional shape of the outlet/supply port of an inhaler/source of medicine. Conforming front end 104, 204 or back end 102, 202 to the cross-sectional shape of the outlet/supply port helps achieve a better fitment and retains tube's 100, 200, 300 airtight gas impermeable nature.

Applicants' extension device/hollow tube 100, 200, 300 described herein is "universal" in that one tube can fit many different inhaler devices, with different cross-section outlet shapes, and does not replace or alter the functionality of any components of an FDA-approved pressurized MDI. Embodiments provide stand-alone hollow extension tubes 100, 200, 300 that are not limited for use with a specific aerosol medication and can be easily adapted for use in any situation that require a disposable mouthpiece for each inhalation.

After the tube 100, 200, 300 (proximal or front end 104, 204 for non-limiting example) is removably coupled (or attached) to the outlet/supply port of a subject inhaler, the inhaler may be actuated with the opposite end (distal or back end 102, 202) of the tube grasped in the user's mouth. Upon actuation, aerosolized medication enters tube 100, 200, 300 at front end 104, 204 and leaves tube 100, 200, 300 from back end 102, 202 after traversing the tube length 110, 210, 310. In other embodiments, tube back end 102, 202 may be removably coupled to the inhaler outlet. Then upon actuation, medicine enters tube 100, 200, 300 at back end 102, 202 and leaves tube 100, 200, 300 at front end 104, 204 after traversing tube length 110, 210, 310.

Extension device tube 100, 200, 300 has such length 110, 210, 310 that the tube sufficiently slows down and reduces the particle size of the plume of medication ejected from an inhaler (more specifically, the actuator as shown in phantom in FIG. 4C) but is not inconvenient to use. In a non-limiting example, medicine enters tube 100, 200, 300 at front end 104, 204 in a roughly conical shaped plume that slows down while expanding inside tube 100, 200, 300 as it travels farther from front end 104, 204. Therefore, length 110, 210, 310 of tube 100, 200, 300 is a careful compromise between two competing objectives—One does not want the tube to be so long that the expanding plume adheres to the interior wall surface 112, 212, but is sufficiently long to slow down the plume for improved drug delivery. Restated the length of the hollow extension tube 100, 200, 300 may be chosen such that there is sufficient space and distance for the medication plume to slow down (decelerate), but not lose so much velocity that the medication spreads into the inner walls of the tube.

The extension device (i.e., tube 100, 200, 300) may be of such dimensions 106, 108, 110, 116, 118, 120, 206, 210, 216, 220, 306, 308, 310 so that it is not inconvenient to the person taking the medication and is a compact, convenient, portable and unobtrusive add-on device to MDIs or other inhalers. Further, users (patients) are able to easily form, with their lips/mouth, a tight seal around the tube 100, 200, 300 end 102, 104, 202, 204 due to the outer circumference (dimensions) and familiar circular, or nearly so, shape as well as deformable material and nature as detailed below.

In particular, the shape of front end 104, 204 and back end 102, 202 of tube 100, 200, 300 presents a familiar circular cross-section to the user. Children are often already familiar with using a drinking straw and controlling the inhalation pressure appropriately. Therefore, presenting them with a hollow extension tube 100, 200, 300 that has a generally circular cross section reduces the need to train the pediatric user and improves technique for improved medication delivery to their lungs, resulting in quicker onset of action and better medical outcomes.

Tube 100, 200, 300 has a fairly (relatively) thin wall-thickness 120, 220 and is sufficiently elastic and semi-rigid to resist deformation when carried in the purse, bag, or on person. But if deformation occurs, either during storage or use, tube 100, 200, 300 is of a wall thickness and material makeup that enable the tube to be reformed to its original or initial cylindrical/conical frustum shape and structure as if the tube had not undergone any deformation. In some embodiments, tube 100, 200, 300 is of sufficiently elastic and/or deformable material and structure (dimensions) that it can be collapsed or flattened for easy storage, carrying, and shipping and quickly returned to its original/initial cylindrical/conical frustum form for use.

Anti-Static Materials and Properties

A key attribute of embodiments of the present invention is the nontoxic, anti-static properties of interior wall surface 112, 212. For example, the interior wall surface 112, 212 may be composed of cardboard or paper. The anti-static properties of interior wall surface 112, 212 reduce the triboelectric effect and static charge buildup inside tube 100, 200, 300. Because interior wall surface 112, 212 is composed of material that is not prone to accumulating static electricity, the amount of medication deposited on interior wall surface 112, 212 of tube 100, 200, 300 is reduced increasing the effectiveness of the delivery system. In some embodiments, interior wall surface 112, 212 may be coated with inert anti-static material that further inhibits medication's potential adhesion to tube's 100, 200, 300 interior wall surface 112, 212.

Spacers and tubes with interior surfaces made of plastic or similar material, as found in the prior art, are prone to accumulating static electrical charge on their inner wall. This static charge causes the medication to adhere to the wall and never reach the patient. The stability, toxicity, interaction between drug and antistatic coatings must be considered when using existing metal or plastic spacer devices as opposed to embodiments of the present invention which utilizes tube 100, 200, 300 with an interior wall surface 112, 212 composed of natural pulp based material such as paper or cardboard.

In some embodiments, the entirety of tube 100, 200, 300 is composed of material not prone to accumulating static electricity. In such embodiments, tube 100, 200, 300 may be coated with a different material, plasticized, or untreated on the outside (exterior wall surface) to improve the grip, sanitation and/or mouth-feel of tube 100, 200, 300. In various embodiments, tube 100, 200, 300 may be constructed of suitable anti-static material that is inexpensive, easily available, suitably robust, and biodegradable or recyclable.

Disposability and Single Use

In embodiments, extension device/tube 100, 200, 300 is designed to be single-use, biodegradable, and easily disposable (non-hazardous waste). By being composed of inexpensive and mass producible material such as cardboard, paper, or similar material, tube 100, 200, 300 is able to be constructed and sold as an efficient single-use product.

Existing holding chambers and spacers are intended for multiple uses, and therefore it is essential that they be kept clean. Manufacturers often recommend washing and air drying after each use. The recommended method for drying existing devices is to air-dry or drip-dry. The user is also instructed to not use any clothing or paper to wipe dry, which can accumulate static electricity due to triboelectric effect and can delay the administration of the next dose of medication. Due to these inherent disadvantages, the patient compliance with manufacturer's instructions is estimated to be low and the cleaning technique suspect at best. In addition, repeated uses and cleaning create a buildup of static and an accumulation of medicine in the holding chamber/spacer which can interfere with the administration of medicine. This can also make the amount of drug reaching the lungs variable, with potentially life-threatening adverse side-effects.

Furthermore, to reduce inhaler wastage among inpatients, some institutions have reported using a common MDI canister protocol. However the use of a common MDI canister among many patients increases the risk of cross-contamination, disease transmission, etc. Contamination that might occur from a common canister protocol would seem to come from the surface of the canister, not the medication itself. In addition, if these medical institutions use some form of a spacer or extension tube at all, they must carry them in sufficient numbers and varieties to fit different inhalers. This increases the cost of inventory and trickles down in the form of increased healthcare costs.

Embodiments of Applicants' invention, by being disposable, avoid the cleaning compliance problems found in the prior art and guarantee a quick maximum effective dose at each use with no sanitation concerns. Because the present invention, in some non-limiting embodiments, is made of inexpensive easily produced material, for example cardboard, it can be sold and produced in bulk at low cost minimizing the financial burden of requiring a new extension device/tube 100, 200, 300 for each dose. Embodiments being single use minimize inadvertent sources of microbial transmission and lower the risk to users including immuno-compromised patients.

Improvements in Usability

Some embodiments may incorporate a flavored coating on the outside surface to improve the mouth-feel or flavor. For instance, the outside surface, along the entire length or on the ends of the tube 100, 200, 300 may be coated with a sweet substance to further reduce the resistance of pediatric patients who may need to use the inhaler with extension device.

Embodiments require the patients to be taught a single breathing technique, as opposed to a number of often conflicting techniques.

Some embodiments may incorporate a flavor, such as beef or chicken, to ease the use of such devices in veterinary practices, for dogs and cats that may need to be treated.

Identifying Marks and Decorative Features

Some embodiments may include markings or decorations on tube 100, 200, 300 exterior. The markings may help a user identify which end 102, 104, 202, 204 to removably couple to an inhaler's outlet/supply port and which end 102, 104, 202, 204 to place in a patient's mouth. The markings may be a dot, small hole, arrow, label, or other indicia or indicator etc., anywhere on tube 100, 200, 300 in any orientation to indicate proper placement on the outlet of the MDI/inhaler.

The tube 100, 200, 300 exterior may also have instructions printed on it and/or be made of one or more colors to enable easier identification and use. The tube 100, 200, 300 exterior may have attractive animals or other illustrations printed on it to assist usage and lower the resistance of pediatric patients to use inhalers, in contrast to unattractive and scary face-masks or other complex spacer devices in the art.

In some embodiments, the tube 100, 200, 300 may be marked in a way to indicate that it has been used, thus indicating the need to replace it for next use of the inhaler with a different person. The indication of use may be accomplished by a coating having temperature changing color or by a nontoxic moisture-sensitive coating. Placing a part of the tube 100, 200, 300 in a patient's mouth will create a temperature and/or moisture change and therefore a corresponding color change of the tube that will indicate a first use.

Telescoping Function

Figure 3A:
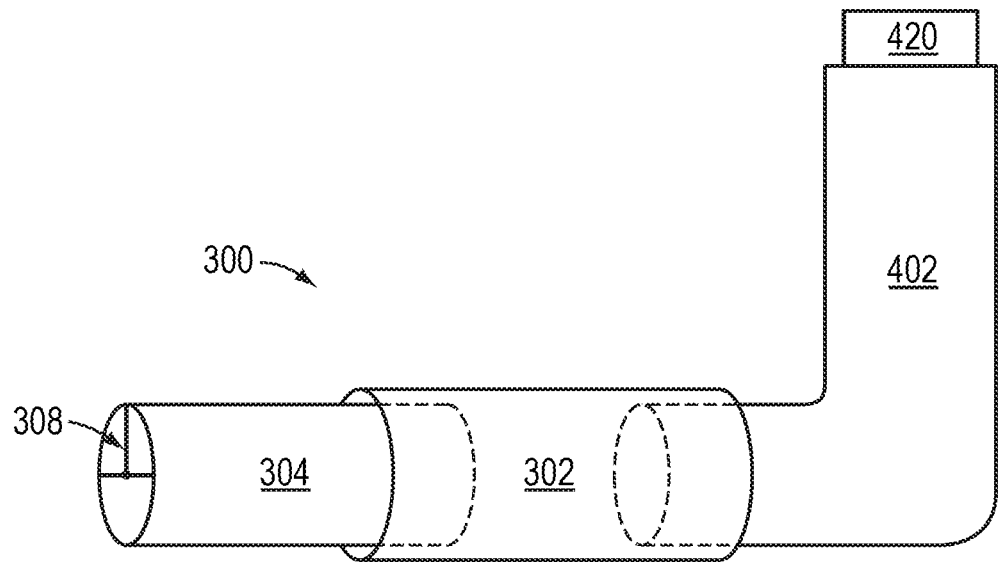
FIGS. 3A and 3B are schematic views of another embodiment comprising telescoping tube parts to achieve variable length.
Figure 3B:
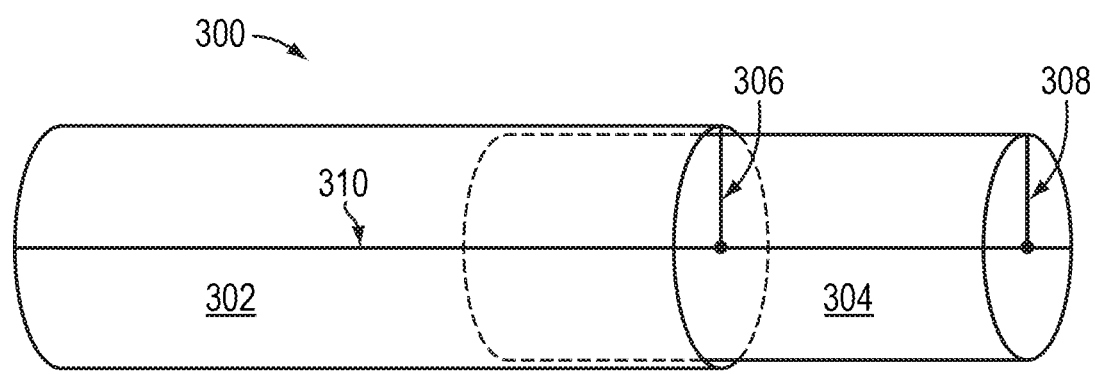

FIGS. 3A and 3B are schematic diagrams of an embodiment with an extension that telescopes to achieve variable length. In such embodiments a tube 300 may be formed of two or more telescoping sections 302, 304 that change effective or operating tube length 310 depending on the user's particular need. Each hollow telescoping section 302, 304 can be shaped as a conical frustum like tube 100 in FIG. 1 or a cylinder like tube 200 in FIG. 2.

Each telescoping section 302, 304 possess a radius 306, 308, respectively. Radius 308 is slightly smaller than radius 306 allowing one section 304 to fit inside the other section 302. The telescoping sections 302, 304 are of different radii to accommodate multiple differently sized inhalers 402.

In some embodiments, the telescoping sections 302, 304 are held together only with friction. In other embodiments, the telescoping sections 302, 304 may have an indentation, groove, ridge, crimping, or other stopping mechanism to prevent the different sections 302, 304 of tube 300 from separating.

Attachment to an Inhaler

Extension device/tube 100, 200, 300 removably couples to the end ("outlet" or "supply port") of an inhaler or other source of medicine. Such coupling is made, depending on the embodiment, at either the front end 104, 204 or the back end 102, 202. Tube 100, 200, 300 can be removably coupled or decoupled to the outlet or supply port of an inhaler through push-on pull-off operation. In some embodiments, the attachment (and detachment) of tube 100, 200, 300 to an inhaler or other source of medicine, requires no clips or other securing mechanisms allowing for quick use and disposal.

When the front end 104, 204 (or back end 102, 202) of tube 100, 200, 300 is pushed onto an outlet of an inhaler, the front end snugly encircles or partially engulfs the outlet. Tube 100, 200, 300 is composed of material sufficiently elastic and/or deformable that the user can easily slightly deform front end 104, 204 to morph and/or conform to the cross-sectional shape of an inhaler outlet. When the front end 104, 204 of tube 100, 200, 300 is pulled off an outlet of an inhaler, the front end 104, 204 reforms to its original shape.

Figure 4A:
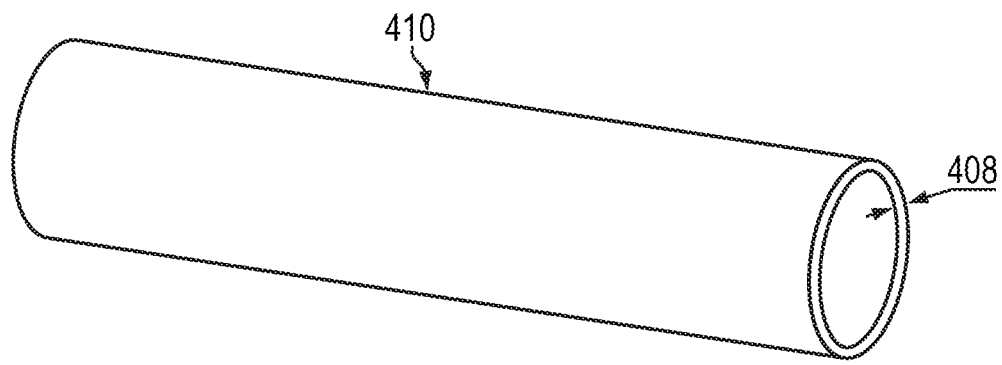
FIG. 4A is a side perspective view of an embodiment.
Figure 4B:
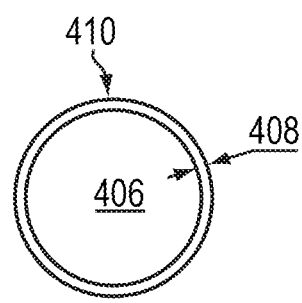
FIG. 4B is a front end view of the FIG. 4A embodiment.
Figure 4C:
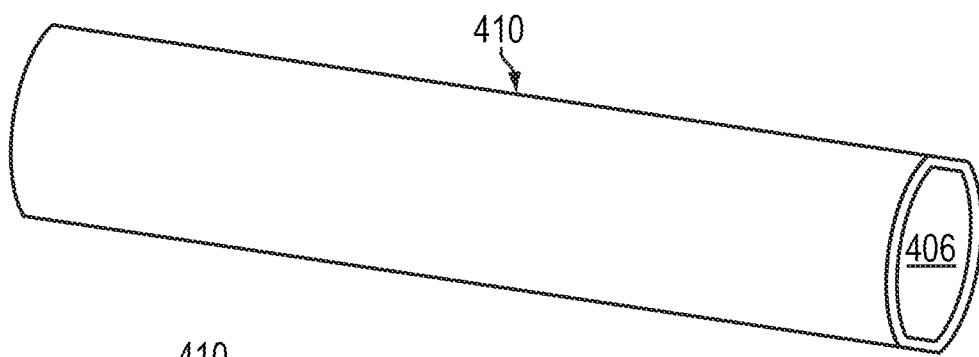
FIG. 4C is a side perspective view of the FIG. 4A embodiment deformed at one end in preparation for assembly with a source of medicine.
Figure 4D:
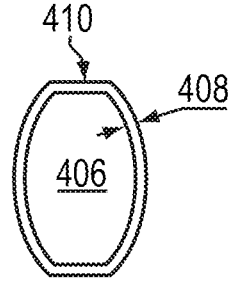
FIG. 4D is a front end view of the FIG. 4C state of the embodiment.

FIGS. 4A-G are schematic diagrams that show a non-limiting example of the coupling of an extension tube (embodying Applicants' present invention) with a source of medicine or gas substance. In an unassembled (uncoupled) and non-deformed state, FIGS. 4A and 4B show a front and side perspective view of extension tube 410 with front end 406 and that has an circular cross section. FIGS. 4C and 4D show a front and side perspective view of extension tube 410 (from FIGS. 4A and 4B) with front end 406 that has been deformed (morphed) from a circular cross section into an oval cross section in preparation for assembly (coupling) with a source of medicine. Tube 410 also possesses relatively thin wall thickness 408 as illustrated in FIGS. 4A-4D and 4G (shown in partial cutaway).

For reference, FIGS. 4E and 4F show side and isometric perspective views of the source of medicine (MDI) 402 with outlet (supply port) 404 that has a roughly oval cross section. MDI 402 contains canister 420 that holds the medicine.

FIG. 4G is a cutaway of tube 410 attached to source of medicine 402 at outlet 404 that illustrates how tube 410 is removably coupled to source of medicine 402. Front end 406 of tube 410 partially engulfs (slips on and encircles) outlet 404 of inhaler 402. Tube 410 is composed of elastic material and possesses wall thickness 408 so that the portion 412 of tube 410 that engulfs/encircles outlet 404 deforms (morphs) to the shape of the exterior of outlet 404 and creates a nearly airtight seal around outlet 404. When tube 410 is removably coupled to outlet 404, front end 406 is deformed into an oval cross section to better fit the oval cross section outlet 404. The attachment of tube 410 to source of medicine 402 can be accomplished by a user pushing them together. Furthermore, tube 410 and source of medicine 402 can be decoupled by a user pulling them apart.

In FIG. 4G, tube 410 and source of medicine 402 stay coupled together because of the force of friction between the exterior surface of outlet 404 and the interior surface of tube front end 406.

In some embodiments, in contrast to FIG. 4G, outlet 404 engulfs or encircles tube front end 406, and portion 412 of tube 410 deforms (morphs) to the shape of the interior surface of outlet 404 instead of the shape of the exterior surface of outlet 404. Flexibly allowing for a connection to be made by tube 410 to source of medicine 402 by being engulfed by outlet 404 or by engulfing outlet 404 increases the number of inhalers and delivery systems that tube 410 can be used with and increases adaptability and versatility.

Example Embodiment

Figure 5:
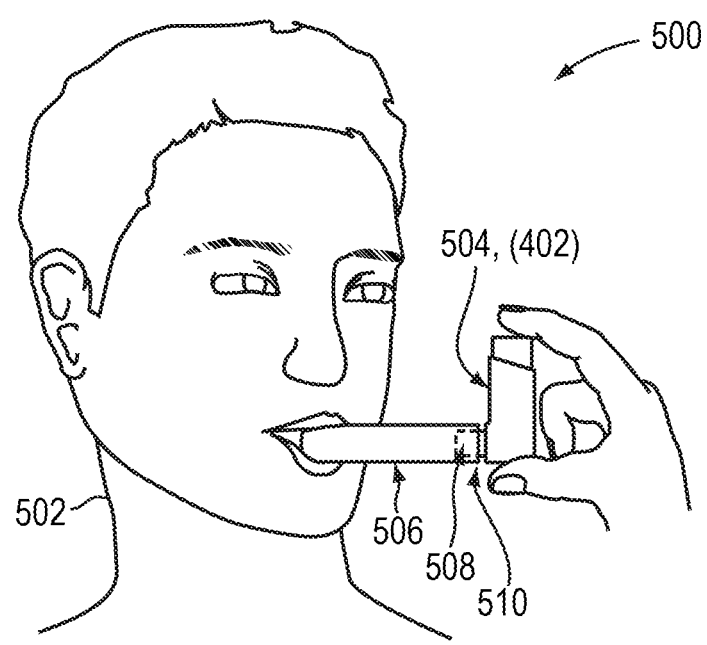
FIG. 5 is a diagram illustrating an embodiment in use with a typical MDI.

FIG. 5 is a diagram illustrating the use of an embodiment of Applicants' invention with a typical MDI 504. One end (the proximal end) 510 of a cylinder shaped extension device tube 506 (such as tube 200 of FIG. 2) is removably coupled to the outlet 508 of MDI 504. The opposite or distal end of tube 506 is placed in the mouth of user/patient 502. This assembly of MDI 504 together with extension tube 506 is used by user/patient 502 to aid in the delivery of a medicament from inhaler 504 to patient's 502 lungs.

Upon actuation of inhaler 504, the aerosolized medication travels out of inhaler 504 at outlet 508 through the anti-static interior of spacer tube 506 into patient's 502 mouth. The ejected plume of aerosolized medication has a velocity that is too high for proper dosing when it exits inhaler 504 at outlet 508. However after traversing the length of tube 506, the velocity of the plume of aerosolized medication is reduced. Tube 506 also effectively allows for more evaporation or sublimation of the propellants and excipients, and reduces the average particle size. Finally, during the duration of traversal, the particle temperature also increases. These effects allow for a greater percentage of the initially ejected amount of medication to reach the patient's 502 lungs and thus achieve more accurate and better dosing. The anti-static interior surface of tube 506 minimizes the amount of aerosolized particles that the tube traps allowing for a reduction in the velocity of the plume of medicine without a reduction in the amount of medicine reaching the patient 502.

Tube 506 is attached (removably coupled) to outlet 508 at tube front end 510 with a push-on motion. Front end 510 partially engulfs or encircles outlet 508. Front end 510 slightly deforms or morphs in order to tightly fit over outlet 508. Because front end 510 snugly fits over outlet 508, no clips or securing mechanisms are needed and tube 506 stays attached to inhaler 504 due to friction force. User 502 can decouple tube 506 by pulling it off outlet 508 and easily discard the one-time use tube 506.

EQUIVALENTS

While this invention has been particularly shown and described with references to example embodiments thereof, it will be understood by those skilled in the art that various changes in form and details may be made therein without departing from the scope of the invention encompassed by the appended claims.

For example, one embodiment of the present invention provides a cardboard extension tube that fits snugly inside or outside an arbitrarily shaped, more commonly circular or oval, actuator outlet. The embodiment can be used in patients of all ages and with several types of inhalers, thus eliminating the need for complex choices on behalf of the prescriber and the user. It is inexpensive, disposable, and portable. Thousands of tubes can easily fit inside a single box. These salient features make it easy to transport and deliver to high-demand areas, including war zones.

The prior art devices are predominantly made of plastic material or metal. These are inherently more expensive than cardboard and do not degrade in regular landfills for thousands of years. Applicants' cardboard extension tubes can be manufactured in large quantities, thus lowering the cost, are environmentally friendly by being biodegradable, and can be easily disposed in household trash, compost pile or recycled with other paper. Further, embodiments are lightweight, portable and can be deployed very rapidly.

Other embodiments of the extension tube 100, 200, 300 may be used anywhere other inhaled substances might be delivered through the upper airway. These other applications are not limited to medication delivery.

As an example, embodiments can be used in hookah lounges, where a hookah might be passed around among multiple people. Use of extension tube 100, 200, 300 as a smoking mouthpiece helps reduce contamination, improves hygiene, and lowers the risk associated with shared mouthpieces. Each user of hookah might be supplied his own extension tube 100, 200, 300 which will minimize the transfer and accumulation of saliva or other bodily fluids. Embodiments may also be used in sensor units that measure alcohol and other drug level in one's breath. Such breath analyzers use of disposable extension tube 100, 200, 300 have the potential to significantly lower the cost of police and law-enforcement organizations that test breath alcohol or drug levels.

As another example, the extension tube may be used to ease the medication delivery for veterinary animals, such as dogs and cats, etc., to efficiently administer aerosolized medicine.

What is claimed is:

1. A device for facilitating the delivery of medicine or other aerosolized substance comprising:

A monolithic hollow gas impermeable tube made of biodegradable cardboard, having a front end spaced across a length of the tube from a back end, wherein the tube has a uniform outer diameter extending from a front end to the back end, the tube removably couplable to a source of medicine at the front end and the back end being placeable inside a patient's mouth, the tube transferring an amount of aerosolized medicine across the length, through an interior space of the tube, from the source of medicine to the patient and the length of the tube providing sufficient space for the aerosolized medicine to decelerate when transferred across the length; the tube having a wall thickness at the front end, the wall thickness being sufficiently thin so that the front end of the tube is effectively elastic and deformable to conform to a cross-sectional shape of a supply port of the source of medicine and be capable of partially engulfing the supply port upon the front end being directly and tightly fitted to the supply port, wherein the front end reforms to an original shape upon removal from the supply port; and the tube having an interior surface forming a wall about the interior space, the cardboard possessing anti-static properties that reduce triboelectric charge buildup.

2. A device as claimed in claim 1 wherein the tube is in the shape of a cylinder.

3. A device as claimed in claim 1 wherein the tube is designed for single use.

4. A device as claimed in claim 1 wherein the front end of the tube is morphable to fit around different shaped supply ports of sources of medicine.

5. A device as claimed in claim 1 wherein the tube is removably coupled to the source of medicine only using a friction force generated between the interior surface of the tube and the supply port.

6. A device as claimed in claim 1 wherein at least one of the back end and the front end of the tube is identified by a visual indicator.

7. A device as claimed in claim 1 wherein the front end of the tube has a diameter that enables the tube to removably couple to the source of medicine by push-on pull-off operation.

\* \* \* \* \*